(12) United States Patent
Mihajlovic

(10) Patent No.: US 11,684,772 B2
(45) Date of Patent: Jun. 27, 2023

(54) ELECTRODE AND METHOD FOR TRANSCRANIAL CURRENT STIMULATION

(71) Applicant: Stichting IMEC Nederland, AE Eindhoven (NL)

(72) Inventor: Vojkan Mihajlovic, Eindhoven (NL)

(73) Assignee: STICHTING IMEC NEDERLAND, AE Eindhoven (NL)

( * ) Notice: Subject to any disclaimer, the term of this patent is extended or adjusted under 35 U.S.C. 154(b) by 0 days.

(21) Appl. No.: 17/318,005

(22) Filed: May 12, 2021

(65) Prior Publication Data
US 2021/0353931 A1    Nov. 18, 2021

(30) Foreign Application Priority Data
May 12, 2020    (EP) .................................... 20174011

(51) Int. Cl.
*A61N 1/36*       (2006.01)
*A61N 1/04*       (2006.01)
(Continued)

(52) U.S. Cl.
CPC ......... *A61N 1/0456* (2013.01); *A61N 1/0476* (2013.01); *A61N 1/36034* (2017.08); *G06F 3/015* (2013.01); *A61N 2001/083* (2013.01)

(58) Field of Classification Search
CPC .............. A61N 1/0456; A61N 1/36034; A61N 1/0476; A61N 2001/083; A61N 1/36025; G06F 3/015
See application file for complete search history.

(56) References Cited

U.S. PATENT DOCUMENTS

| 9,014,811 B2 | 4/2015 | Pal et al. |
| 2006/0173510 A1 | 8/2006 | Besio et al. |

(Continued)

FOREIGN PATENT DOCUMENTS

| GB | 2541947 A | 8/2017 |
| GB | 2577534 A | 1/2020 |
| WO | WO2016/132215 A1 | 8/2016 |

OTHER PUBLICATIONS

Mora Lopez et al: "An Implantable 455-Active-Electrode 52-Channel CMOS Neural Probe", IEEE Journal of Solid-State Circuits, vol. 49, No. 1, pp. 248-261, Jan. 2014.
(Continued)

*Primary Examiner* — Ankit D Tejani
*Assistant Examiner* — Joshua Brendon Solomon
(74) *Attorney, Agent, or Firm* — Moser Taboada

(57) ABSTRACT

An electrode (10) for transcranial current stimulation is provided. The electrode (10) comprises at least two pins (11*a*, 11*b*) for contacting the skin of a living or human being, and a current delivering unit (12) connected to the at least two pins (11*a*, 11*b*). The current delivering unit (12) is configured to estimate the corresponding range of the respective contact impedance with respect to the skin for each of the at least two pins (11*a*, 11*b*) or to analyze the corresponding level of the respective contact impedance with respect to the skin for each of the at least two pins (11*a*, 11*b*). The current delivering unit (12) is configured to distribute a desired current over all of the at least two pins (11*a*, 11*b*) or to select a set of the at least two pins (11*a*, 11*b*) for delivering a set of partial currents in order to achieve the desired current.

20 Claims, 7 Drawing Sheets

(51) Int. Cl.
*G06F 3/01* (2006.01)
*A61N 1/08* (2006.01)

(56) References Cited

U.S. PATENT DOCUMENTS

| | | | |
|---|---|---|---|
| 2014/0148872 A1* | 5/2014 | Goldwasser | A61N 1/36034 |
| | | | 607/45 |
| 2014/0309714 A1 | 10/2014 | Mercanzini et al. | |
| 2015/0224311 A1 | 8/2015 | Yun et al. | |
| 2016/0150992 A1 | 6/2016 | Lee | |
| 2017/0165485 A1* | 6/2017 | Sullivan | A61B 5/0022 |
| 2018/0345006 A1* | 12/2018 | Ambrose | A61N 1/0476 |
| 2019/0059803 A1* | 2/2019 | Myers | A61B 5/746 |
| 2019/0343462 A1* | 11/2019 | Grant | A61B 5/24 |

OTHER PUBLICATIONS

Extended European Search Report in EP20174011.5 dated Oct. 14, 2020.

* cited by examiner

| Vo_high | Vo_low | R_ETI |
|---|---|---|
| 1 | 1 | >R_low, <R_high |
| 1 | 0 | <R_low |
| 0 | 1 | >R_high |
| 0 | 0 | N/A |

ELECTRODE AND METHOD FOR TRANSCRANIAL CURRENT STIMULATION

CROSS REFERENCE TO RELATED APPLICATION

This application claims priority to EPC Application No. 20174011.5, filed on May 12, 2020, which is incorporated herein by reference in its entirety.

The invention relates to an electrode for transcranial current stimulation and a method for transcranial current stimulation.

Generally, in times of an increasing number of medical applications providing transcranial current stimulation, there is a growing need of an electrode for transcranial current stimulation and a method for transcranial current stimulation, which ensure a safe, accurate, and efficient stimulation.

US 2016/0150992 A1 relates to an electronic device for measuring EEG (electroencephalography) signal or electronic stimulation. Said device includes electrode modules, attached to each different position of the head of the subject, measuring an EEG signal from the head or applying current to the head, each of which is including microelectrodes forming an electrode array. A control module controls each of the electrode modules for measuring an EEG signal from the subject's head or applying current thereto. An EEG signal processing module processes an EEG signal detected by the electrode modules and an electric stimulation module provides the electrode modules with a current for electric stimulation. Disadvantageously, especially due to a lack of any impedance measurement with respect to the corresponding contact impedance regarding the skin, safety, accuracy, and efficiency cannot be guaranteed.

Accordingly, there is an object to provide an electrode for transcranial current stimulation and a method for transcranial current stimulation, thereby ensuring a particularly high safety, accuracy and efficiency of the stimulation.

This object is solved by the features of the first independent claim for an electrode for transcranial current stimulation and the features of the second independent claim for a method for transcranial current stimulation. The dependent claims contain further developments.

According to a first aspect of the invention, an electrode for transcranial current stimulation is provided. The electrode comprises at least two pins for contacting the skin of a living or human being, and a current delivering unit connected to the at least two pins. In this context, the current delivering unit is configured to estimate the corresponding range of the respective contact impedance with respect to the skin for each of the at least two pins or to analyze the corresponding level of the respective contact impedance with respect to the skin for each of the at least two pins. In addition to this, the current delivering unit is configured to distribute a desired current over all of the at least two pins or to select a set of the at least two pins for delivering a set of partial currents in order to achieve the desired current, in each case on the basis of the estimated corresponding range of the respective contact impedance with respect to the skin for each of the at least two pins or on the basis of the analyzed corresponding level of the respective contact impedance with respect to the skin for each of the at least two pins. Advantageously, safety, accuracy, and efficiency can be ensured.

According to a first preferred implementation form of the first aspect of the invention, the current delivering unit is directly integrated into the electrode. Advantageously, flexibility can be increased, thereby also increasing efficiency.

According to a second preferred implementation form of the first aspect of the invention, the desired current is predefined especially by a user. In addition to this or as an alternative, the current delivering unit is configured to select the set of the at least two pins in a manner that the corresponding contact impedance of at least one, preferably of each, pin of said set with respect to the skin is lower than a predefined contact impedance value. Advantageously, complexity can be reduced, which leads to an increased efficiency.

According to a further preferred implementation form of the first aspect of the invention, the current delivering unit comprises at least one safety trigger, preferably a safety trigger for each of the at least two pins, wherein each safety trigger is configured to deactivate the corresponding pin if the respective current density with respect to the skin exceeds a predefined current density value. Advantageously, safety can further be increased.

According to a further preferred implementation form of the first aspect of the invention, the current delivering unit comprises at least one amplifier, preferably an amplifier for each of the at least two pins, wherein each amplifier is configured to amplify the corresponding skin potential signal of the respective pin for estimating the corresponding range of the respective contact impedance or for analyzing the corresponding level of the respective contact impedance. Advantageously, accuracy can further be increased.

According to a further preferred implementation form of the first aspect of the invention, the current delivering unit comprises at least one analog-to-digital converter, preferably an analog-to-digital converter for each of the at least two pins, wherein each analog-to-digital converter is configured to digitize the corresponding skin potential signal of the respective pin or, especially in the case of the usage of the at least one amplifier, said signal after amplification. Advantageously, complexity can further be reduced, which leads to an increased efficiency.

According to a further preferred implementation form of the first aspect of the invention, the current delivering unit comprises a digital signal processor, wherein the digital signal processor is configured to perform signal processing operations and/or calculations in order to estimate the corresponding range of the respective contact impedance with respect to the skin for each of the at least two pins or to analyze the corresponding level of the respective contact impedance with respect to the skin for each of the at least two pins. In addition to this or as an alternative, the digital signal processor is configured to control the respective current delivery. Further additionally or further alternatively, the digital signal processor may be configured to control the at least one, preferably each, safety trigger. In further addition to this or as a further alternative, the digital signal processor may be configured to receive the corresponding output signal of the at least one, preferably of each, analog-to-digital converter for performing the signal processing operations and/or the calculations. Advantageously, safety, accuracy, and efficiency can further be increased.

According to a further preferred implementation form of the first aspect of the invention, the current delivering unit comprises a communication unit, wherein the communication unit is configured to transmit the corresponding results of estimating the corresponding range of the respective contact impedance with respect to the skin for each of the at least two pins or of analyzing the corresponding level of the respective contact impedance with respect to the skin for each of the at least two pins especially to a back-end unit. In addition to this or as an alternative, the communication unit may be configured to transmit the corresponding status of the at least one, preferably of each, safety trigger to the back-end unit. Advantageously, flexibility can further be increased, thereby increasing efficiency.

According to a further preferred implementation form of the first aspect of the invention, the communication unit is configured to receive configuration data for configuring the current delivering unit especially from the back-end unit. Advantageously, efficiency can further be increased.

According to a further preferred implementation form of the first aspect of the invention, the respective communication with the aid of the communication unit is based on a wireline communication, preferably employing at least one of serial peripheral interface, inter-integrated circuit, or universal asynchronous receiver transmitter. In addition to this or as an alternative, the respective communication with the aid of the communication unit is based on a wireless communication, preferably employing at least one of Bluetooth, especially Bluetooth low energy, wireless local area network, or ZigBee. Advantageously, inefficiencies can further be reduced by increasing flexibility.

According to a further preferred implementation form of the first aspect of the invention, the electrode is used for recording an electroencephalography. Advantageously, flexibility can further be increased, which leads to an increased efficiency.

According a second aspect of the invention, a method for transcranial current stimulation is provided. The method comprises the steps of contacting the skin of a living or human being with the aid of at least two pins of an electrode, estimating the corresponding range of the respective contact impedance with respect to the skin for each of the at least two pins or analyzing the corresponding level of the respective contact impedance with respect to the skin for each of the at least two pins with the aid of a current delivering unit connected to the at least two pins, and distributing a desired current over all of the at least two pins or selecting a set of the at least two pins for delivering a set of partial currents in order to achieve the desired current with the aid of the current delivering unit, in each case on the basis of the estimated corresponding range of the respective contact impedance with respect to the skin for each of the at least two pins or on the basis of the analyzed corresponding level of the respective contact impedance with respect to the skin for each of the at least two pins. Advantageously, safety, accuracy, and efficiency can be ensured.

According to a first preferred implementation form of the second aspect of the invention, the method further comprises the step of co-integrating the at least two pins and the current delivering unit into the electrode. Advantageously, flexibility can be increased, thereby also increasing efficiency.

According to a second preferred implementation form of the second aspect of the invention, the method further comprises the steps of predefining the desired current especially by a user, and/or selecting the set of the at least two pins in a manner that the corresponding contact impedance of at least one, preferably of each, pin of said set with respect to the skin is lower than a predefined contact impedance value. Advantageously, complexity can be reduced, which leads to an increased efficiency.

Exemplary embodiments of the invention are now further explained with respect to the drawings by way of example only, and not for limitation. In the drawings.

Figure 1:
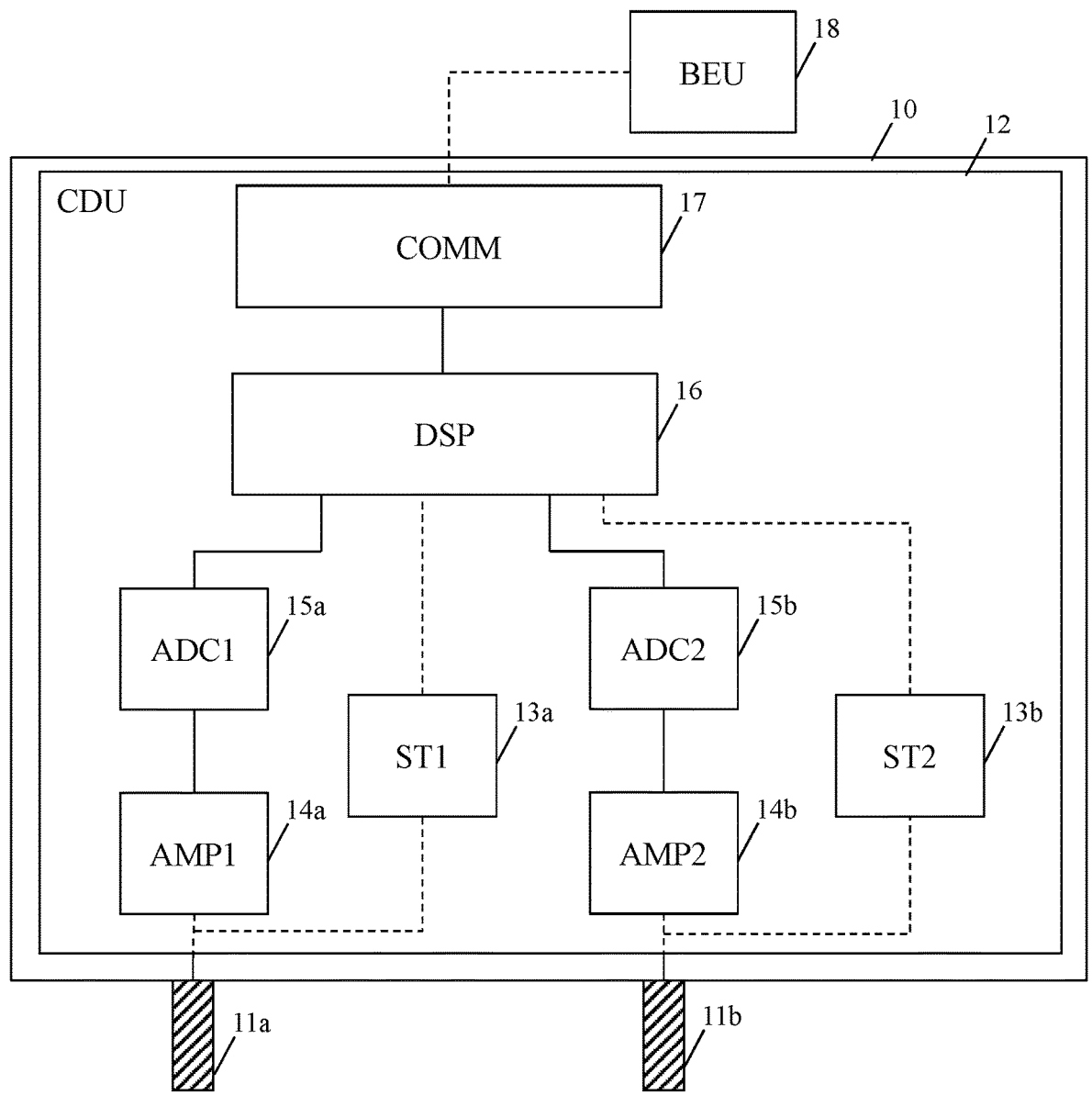
FIG. 1 shows a first exemplary embodiment of an inventive electrode for transcranial current stimulation.

With respect to FIG. 1, a block diagram of an exemplary embodiment of an electrode 10 for transcranial current stimulation is shown.

As it can be seen, the electrode 10 for transcranial current stimulation comprises at least two pins, exemplarily two pins 11a, 11b, for contacting the skin of a living or human being, and a current delivering unit 12 connected to the exemplary two pins 11a, 11b. In this context, the current delivering unit 12 is configured to estimate the corresponding range of the respective contact impedance with respect to the skin for each of the exemplary two pins 11a, 11b or to analyze the corresponding level of the respective contact impedance with respect to the skin for each of the exemplary two pins 11a, 11b.

In addition to this, the current delivering unit 12 is configured to distribute a desired current over all of the exemplary two pins 11a, 11b or to select a set of the exemplary two pins 11a, 11b for delivering a set of partial currents in order to achieve the desired current, in each case on the basis of the estimated corresponding range of the respective contact impedance with respect to the skin for each of the exemplary two pins 11a, 11b or on the basis of the analyzed corresponding level of the respective contact impedance with respect to the skin for each of the exemplary two pins 11a, 11b.

As it can further be seen from FIG. 1, advantageously, the current delivering unit 12 is directly integrated into the electrode 10. With respect to the above-mentioned desired current, it is noted that the desired current may preferably be predefined especially by a user. In addition to this or as an alternative, the current delivering unit 12 may be configured to select the set of the exemplary two pins 11a, 11b in a manner that the corresponding contact impedance of at least one, preferably of each, pin of said set with respect to the skin is lower than a predefined contact impedance value.

Furthermore, the current delivering unit 12 comprises at least one safety trigger, exemplarily a safety trigger 13a, 13b for each of the exemplary two pins 11a, 11b. In this context, each safety trigger 13a, 13b is configured to deactivate the corresponding pin if the respective current density with respect to the skin exceeds a predefined current density value.

It might be particularly advantageous if the predefined current density value is between 2337 and 2549 micro-amperes per square centimeter or between 581 and 637 micro-amperes per square centimeter or between 67 and 80 micro-amperes per square centimeter, preferably between 51 and 57 micro-amperes per square centimeter. It is further noted that it might be particularly advantageous to use the respective upper limit or the respective lower limit of each of said ranges.

Moreover, the current delivering unit 12 comprises at least one amplifier, exemplarily an amplifier 14a, 14b for each of the exemplary two pins 11a, 11b. In this context, each amplifier 14a, 14b is configured to amplify the corresponding skin potential signal of the respective pin for estimating the corresponding range of the respective contact impedance or for analyzing the corresponding level of the respective contact impedance.

It is further noted that the current delivering unit 12 comprises at least one analog-to-digital converter, exemplarily an analog-to-digital converter 15a, 15b for each of the exemplary two pins. In this context, each analog-to-digital converter 15a, 15b is configured to digitize the corresponding skin potential signal of the respective pin or, exemplarily, said signal after amplification.

Furthermore, the current delivering unit 12 comprises a digital signal processor 16, wherein the digital signal processor 16 is configured to perform signal processing operations and/or calculations in order to estimate the corresponding range of the respective contact impedance with respect to the skin for each of the exemplary two pins 11a, 11b or to analyze the corresponding level of the respective contact impedance with respect to the skin for each of the exemplary two pins 11a, 11b.

In addition to this or as an alternative, the digital signal processor 16 is configured to control the respective current delivery. Further additionally or further alternatively, the digital signal processor 16 is configured to control the at least one, exemplarily each safety trigger 13a, 13b.

In further addition to this or as a further alternative, the digital signal processor 16 is configured to receive the corresponding output signal of the at least one, exemplarily of each analog-to-digital converter 15a, 15b for performing the signal processing operations and/or the calculations.

As it can further be seen from FIG. 1, the current delivering unit 12 comprises a communication unit 17. In this context, the communication unit 17 is configured to transmit the corresponding results of estimating the corresponding range of the respective contact impedance with respect to the skin for each of the exemplary two pins 11a, 11b or of analyzing the corresponding level of the respective contact impedance with respect to the skin for each of the exemplary two pins 11a, 11b especially to a back-end unit 18.

In addition to this or as an alternative, the communication unit 17 is configured to transmit the corresponding status of the at least one, exemplarily of each safety trigger 13a, 13b especially to the back-end unit 18. In this context, the communication unit 17 may preferably be configured to receive configuration data for configuring the current delivering unit 12 especially from the back-end unit 18.

It might be particularly advantageous if the respective communication with the aid of the communication unit 17 is based on a wireline communication, preferably employing at least one of serial peripheral interface (SPI), inter-integrated circuit (I2C), or universal asynchronous receiver transmitter (UART). In addition to this or as an alternative, the respective communication with the aid of the communication unit 17 is based on a wireless communication, preferably employing at least one of Bluetooth, especially Bluetooth low energy (BLE), wireless local area network (WLAN), or ZigBee.

It is further noted that the electrode 10 is preferably used for recording an electroencephalography (EEG). With respect to each of the second embodiment according to FIG. 2, the third embodiment according to FIG. 3, and the fourth embodiment according to FIG. 4, said capability of EEG recording is illustrated by a respective EEG-path EEG1, EEG2, ..., EEGn for the corresponding pin 11a, 11b, ..., 11N especially in addition to the respective contact impedance estimating or analyzing path IMP1, IMP2, ..., IMPn for the corresponding pin 11a, 11b, ..., 11N. Preferably, for each of the pins 11a, 11b, ..., 11N, said different paths for recording an EEG and estimating or analyzing the respective contact impedance are parallel paths.

In this context, it is additionally noted that for each of the pins 11a, 11b, ..., 11N, an additional analog-to-digital converter 25a, 25b, ..., 25N is provided especially for digitizing the corresponding signal for EEG recording. Accordingly, it might be particularly advantageous if the current delivering unit 12 of the first embodiment comprises two analog-to-digital converters preferably for each of the pins.

Figure 2:
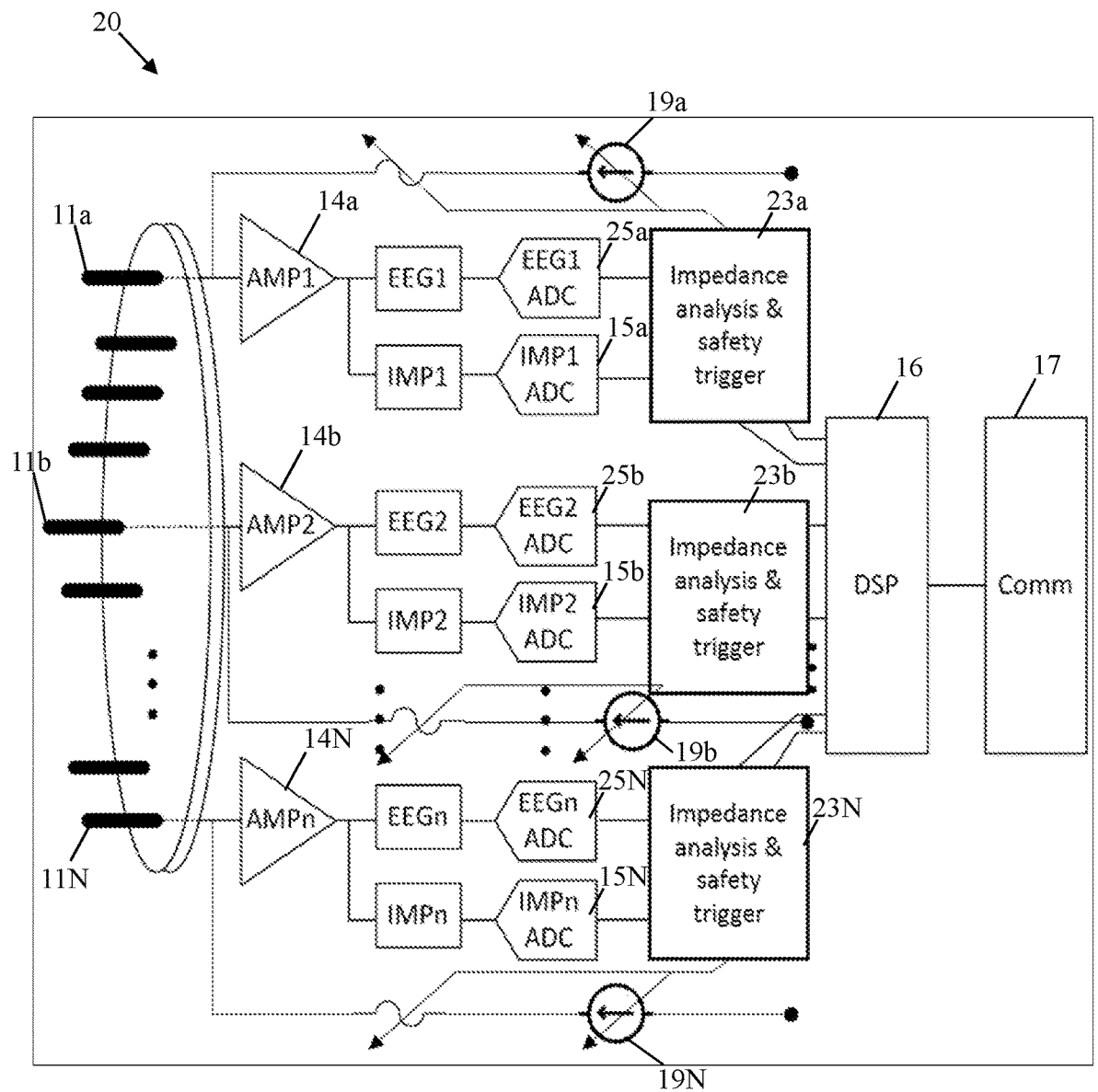
FIG. 2 shows a second exemplary embodiment of an inventive electrode.

Now, with respect to FIG. 2, it is noted that contact impedance estimation or analysis and the safety trigger mentioned in the context of FIG. 1 are combined in a respective impedance analysis and safety trigger unit 23a, 23b, ..., 23N for each of the pins 11a, 11b, ..., 11N. Furthermore, each of the pins 11a, 11b, ..., 11N is connected to a corresponding current source 19a, 19b, ..., 19N for current delivery.

It is further noted that each of the pins 11a, 11b, ..., 11N can be disconnected from the corresponding current source 19a, 19b, ..., 19N by the respective impedance analysis and safety trigger unit 23a, 23b, ..., 23N if this is required.

Moreover, the second embodiment according to FIG. 2 may be summarized as an embodiment comprising active circuitry per pin that estimates the range of contact impedance and has a kind of fuse (said disconnecting by the respective unit 23a, 23b, ..., 23N) that disables as soon as the current delivery becomes higher than certain value combined with active multipin circuitry that delivers specified current that is distributed over all the pins.

Figure 3:
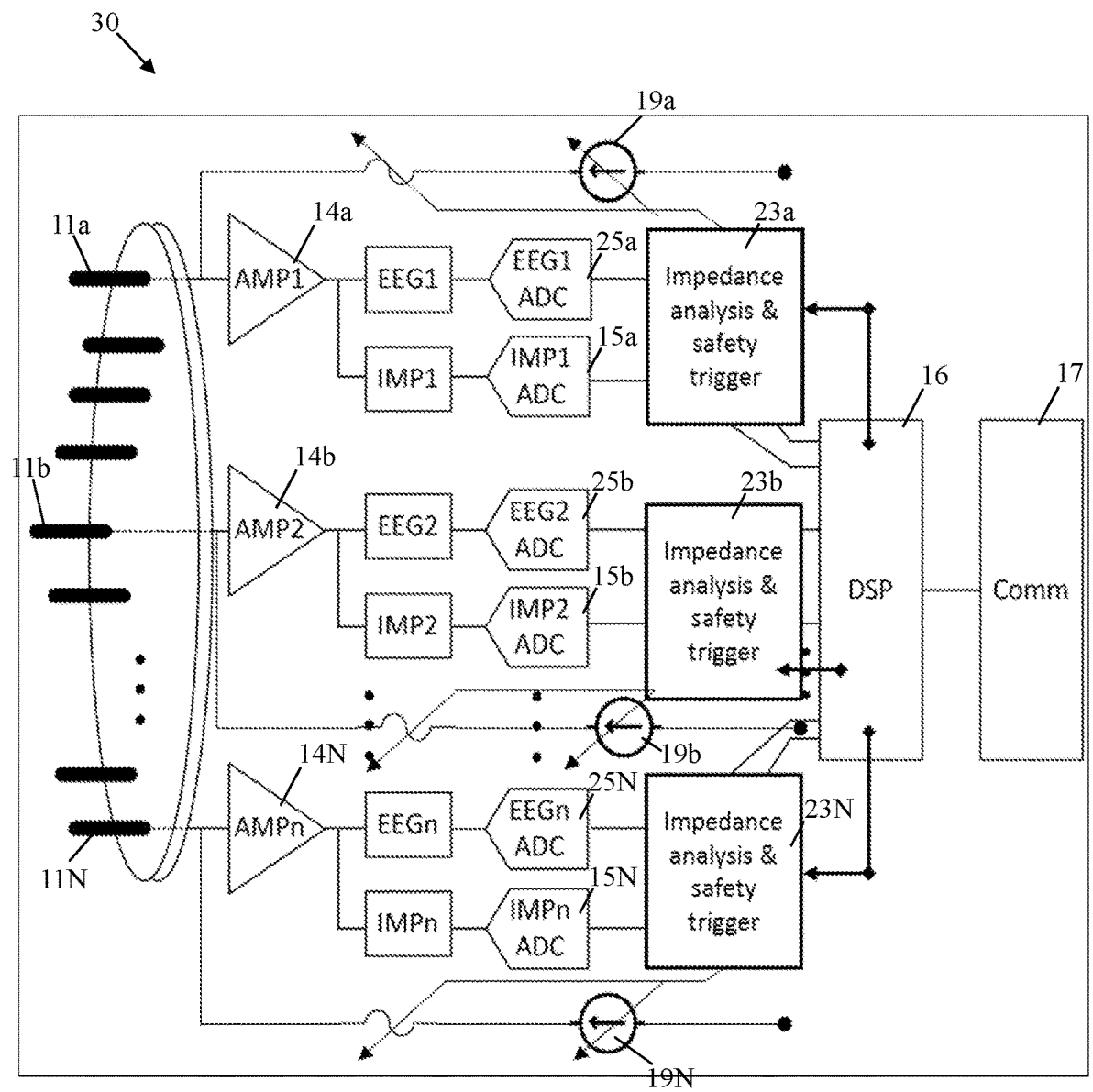
FIG. 3 shows a third exemplary embodiment of an inventive electrode.

Now, with respect to FIG. 3, the third embodiment may be summarized as an embodiment comprising an active circuitry per pin that estimates the range of contact impedance and has a kind of fuse (said disconnecting by the respective unit 23a, 23b, ..., 23N) that disables as soon as the current delivery becomes higher than a certain value combined with active multipin circuitry (with optionally software implementation) that receives the information on contact impedance per pin and selects the minimum or optimal set of pins to which to deliver the current to achieve specified current.

Accordingly, the third embodiment especially differs from the second embodiment in that the third embodiments allows for an individual current injection with respect to each of the pins 11a, 11b, ..., 11N, which is illustrated by the arrows between the digital signal processor 16 and the impedance analysis and safety trigger units 23a, 23b, ..., 23N. Said arrows especially illustrate that said units 23a, 23b, ..., 23N are individually controlled by the digital signal processor 16.

Figure 4:
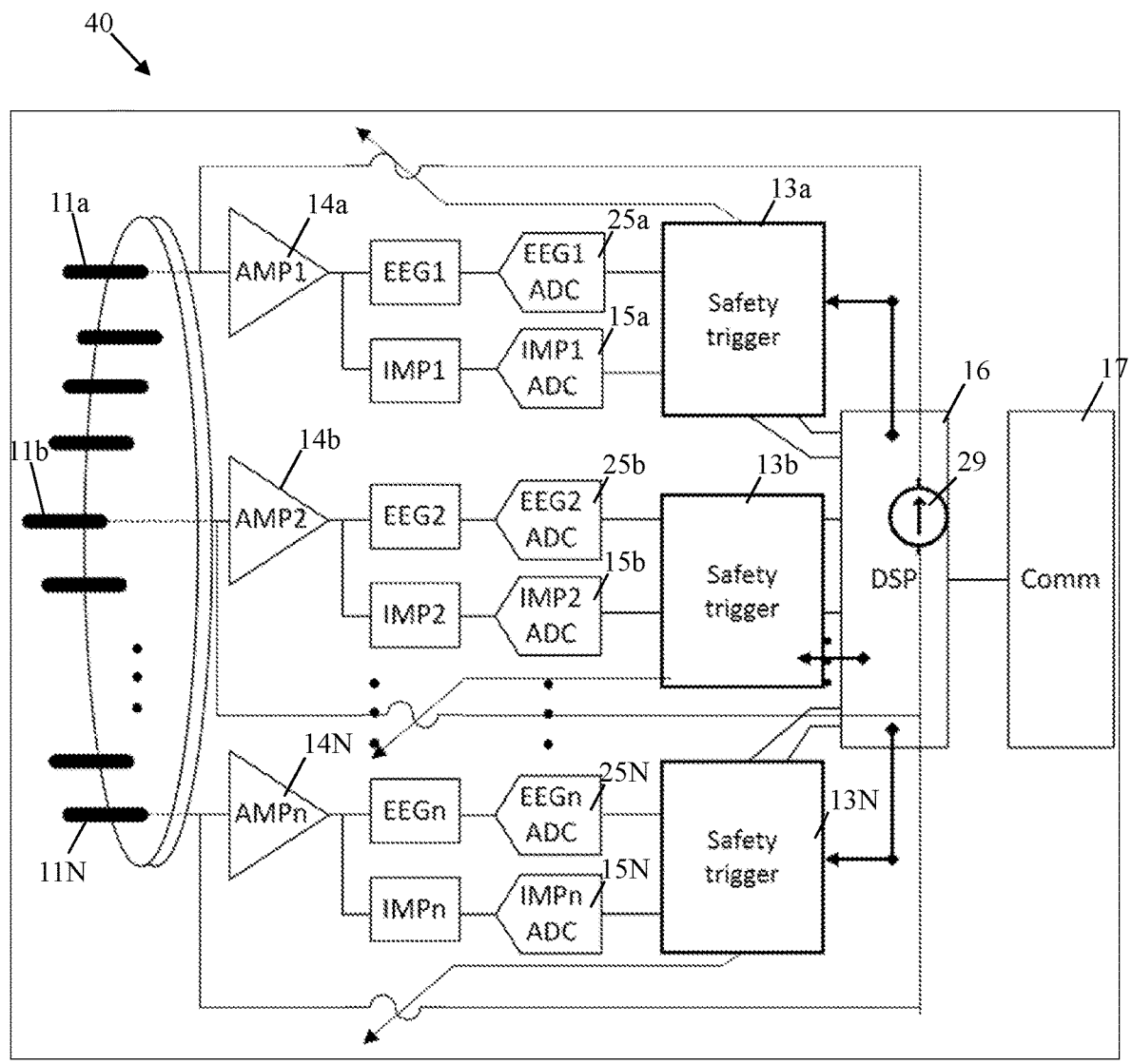
FIG. 4 shows a fourth exemplary embodiment of an inventive electrode.

Now, with respect to FIG. 4, the fourth embodiment comprises only one current source 29, preferably a central current source, being especially comprised by the digital signal processor 16. Preferably, said current source 29 is connected to each of the pins 11a, 11b, ..., 11N.

Furthermore, the fourth embodiment according to FIG. 4 may be summarized as an embodiment comprising active circuitry per pin that acquires the impedance and has a kind of fuse (disconnecting the respective connection path between the current source 29 and the corresponding pin 11a, 11b, ..., 11N by the respective safety trigger 13a, 13b, ..., 13N being especially controlled by the digital signal processor 16) that disables as soon as the current delivery becomes higher than certain value combined with active multipin circuitry (with optionally software implementation) that estimates the information on the exact contact impedance per pin and selects the minimum or optimal set of pins to which to deliver current to achieve a specified current.

It is further noted that said kind of a fuse in the embodiments above can be also part of the multipin electrode circuitry instead of pin active circuitry. Furthermore, the complete circuitry can be realized as multipin circuitry handling the per pin input.

Moreover, with respect to each of the embodiments according to FIG. 1, FIG. 2, FIG. 3, and FIG. 4, it may generally be noted that it might be particularly advantageous if, especially to facilitate exact current stimulation, the common circuitry for the (multipin) electrode would have to perform at least the following critical operations:

Deliver the required level of current being especially predefined by a user, using the available number of pins, preferably dry pins, with relatively low contact impedance.

Deliver currents only to pins that can produce safe level of currents producing current densities lower than the maximum prescribed current density per pin are delivered.

Figure 5:
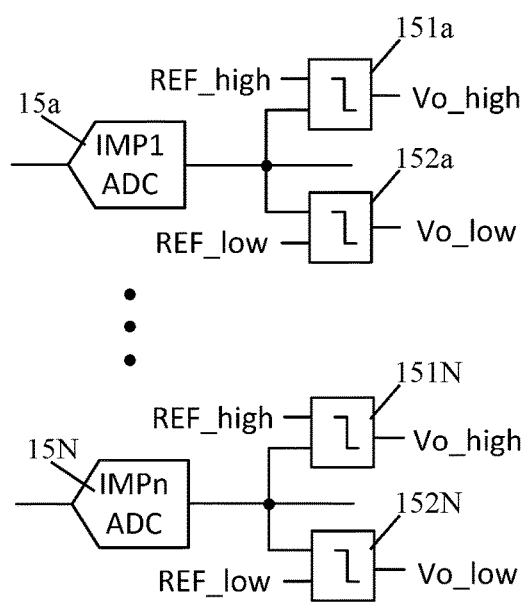
FIG. 5 shows an exemplary contact impedance analyzing circuit for a pin of an inventive electrode.

In accordance with FIG. 5, an exemplary contact impedance analyzing circuit for a pin 11a, 11b, ..., 11N of the electrode 10, 20, 30, 40 according to any of the embodiments according to FIG. 1, FIG. 2, FIG. 3, and FIG. 4 is shown.

As it can be seen from FIG. 5, said analyzing circuit comprises two comparators 151a, ..., 151N and 152a, ..., 152N for each pin 11a, 11b, ..., 11N, both especially connected to an output of the respective analog-to-digital converter 15a, ..., 15N preferably for digitizing the corresponding skin potential signal of the respective pin 11a, 11b, ..., 11N or said signal after amplification, respectively.

It is noted that one 151a, ..., 151N of each two comparators is configured to compare the respective digitized signal with an upper reference voltage, whereas the other one 152a, ..., 152N of said two comparators per pin 11a, ..., 11N is configured to compare said respective digitized signal to a lower reference voltage. The corresponding decision table is also illustrated with the aid of FIG. 5.

Figure 6:
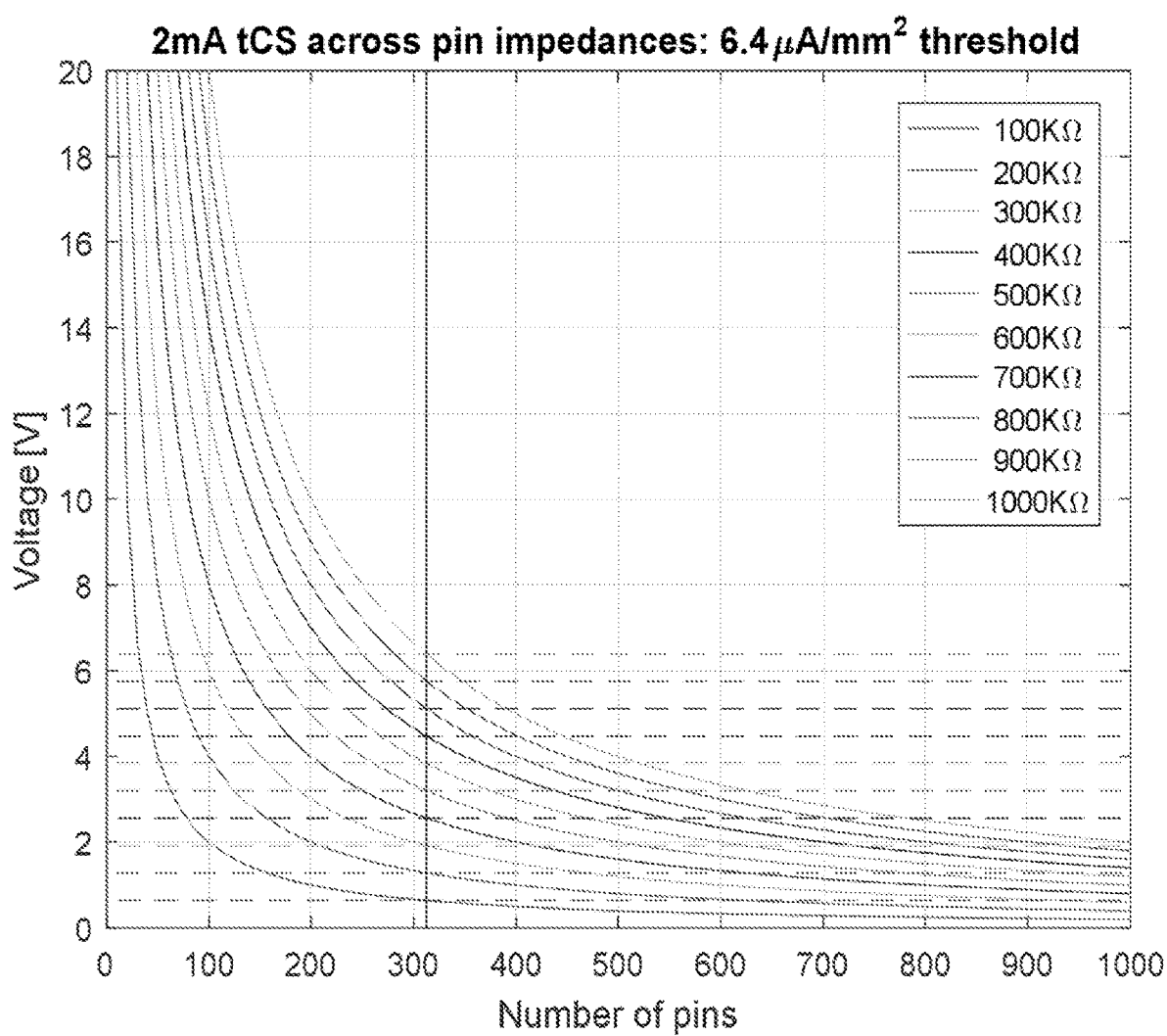
FIG. 6 shows an exemplary diagram with respect to the number of pins required for an inventive electrode.

Moreover, with respect to FIG. 6, an exemplary diagram with respect to the number of pins required for an inventive electrode is illustrated. In this context, a pin contact surface of 1 square millimeter has been assumed. It is noted that the respective contact surface of each of the pins 11a, ..., 11N of the above-mentioned embodiments is preferably between 0.75 and 1.25 square millimeter, more preferably between 0.9 and 1.1 square millimeters.

Preferably, the contact impedance of each pin 11a, ..., 11N is to be between 100 kilo-ohms and 1 megaohm. Furthermore, currents of 2 milli-amperes with current density below 637 micro-amperes per square centimeter can be realized by an inventive electrode, preferably a dry electrode, comprising 314 pins as shown in FIG. 6. It is noted that the inventive electrode comprises preferably between 250 and 350 pins, more preferably between 280 and 330 pins, most preferably between 310 and 320 pins.

Figure 7:
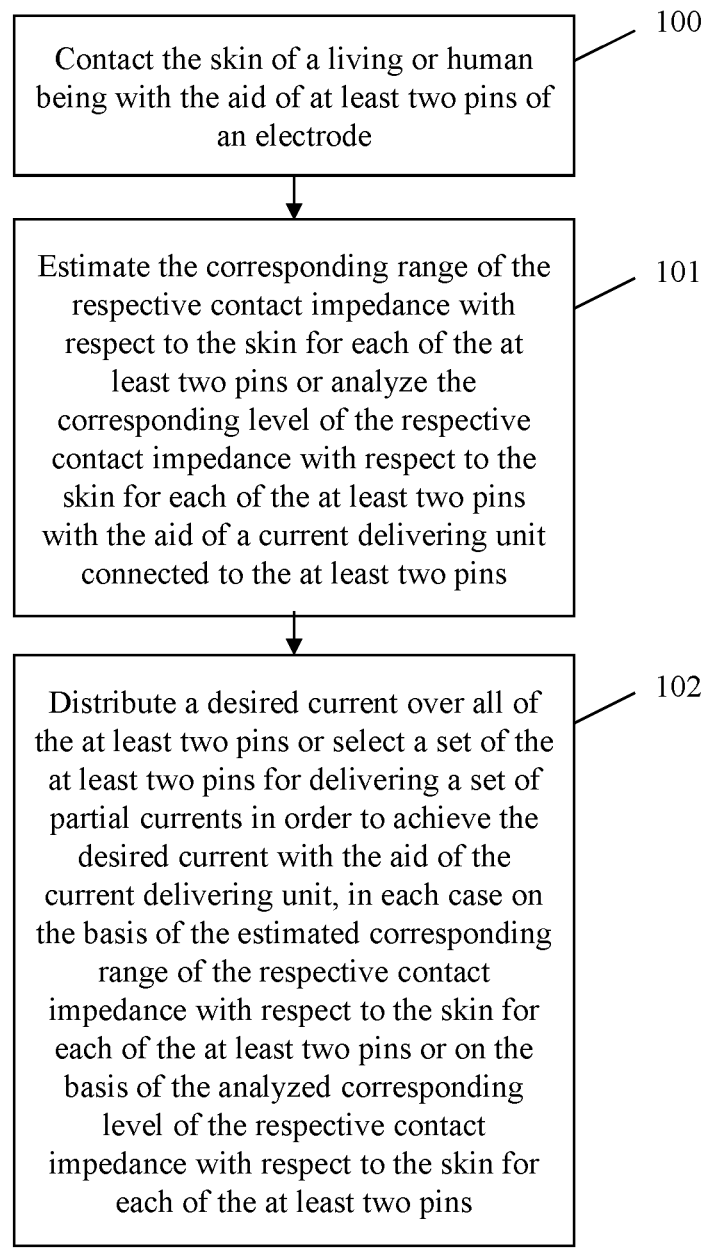
FIG. 7 shows a flow chart of an embodiment of the second aspect of the invention.

Finally, FIG. 7 shows a flow chart of an embodiment of the inventive method for transcranial current stimulation. In a first step 100, the skin of a living animal or human being is contacted with the aid of at least two pins of an electrode. Then, in a second step 101, the corresponding range of the respective contact impedance with respect to the skin is estimated for each of the at least two pins or the corresponding level of the respective contact impedance with respect to the skin is analyzed for each of the at least two pins with the aid of a current delivering unit connected to the at least two pins. Furthermore, in a third step 102, a desired current is distributed over all of the at least two pins or a set of the at least two pins is selected for delivering a set of partial currents in order to achieve the desired current with the aid of the current delivering unit, in each case on the basis of the estimated corresponding range of the respective contact impedance with respect to the skin for each of the at least two pins or on the basis of the analyzed corresponding level of the respective contact impedance with respect to the skin for each of the at least two pins.

It is noted that it might be particularly advantageous if the method further comprises the step of co-integrating the at least two pins and the current delivering unit into the electrode.

Further advantageously, the method may further comprise the step of predefining the desired current especially by a user. In addition to this or as an alternative, the method may comprise the step of selecting the set of the at least two pins in a manner that the corresponding contact impedance of at least one, preferably of each, pin of said set with respect to the skin is lower than a predefined contact impedance value.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The invention claimed is:

1. An electrode for transcranial current stimulation, the electrode comprising:
   at least two pins for contacting the skin of a living or human being, and
   a current delivering unit connected to the at least two pins,
   wherein the current delivering unit is configured to estimate the corresponding range of the respective contact impedance with respect to the skin for each of the at least two pins or to analyze the corresponding level of the respective contact impedance with respect to the skin for each of the at least two pins, and
   wherein the current delivering unit is configured to select a set of the at least two pins for delivering a set of partial currents to achieve the desired current based on the estimated corresponding range of the respective contact impedance with respect to the skin for each of the at least two pins or based on the analyzed corresponding level of the respective contact impedance with respect to the skin for each of the at least two pins.

2. The electrode according to claim 1,
   wherein the current delivering unit is directly integrated into the electrode.

3. The electrode according to claim 1,
wherein the desired current is predefined by user, and
wherein the current delivering unit is configured to select the set of the at least two pins in a manner that the corresponding contact impedance of at least one pin of said set with respect to the skin is lower than a predefined contact impedance value.

4. The electrode according to claim 1,
wherein the current delivering unit comprises at least one safety trigger,
wherein each safety trigger is configured to deactivate the corresponding pin if the respective current density with respect to the skin exceeds a predefined current density value.

5. The electrode according to claim 1,
wherein the current delivering unit comprises at least one amplifier,
wherein each amplifier is configured to amplify the corresponding skin potential signal of the respective pin for estimating the corresponding range of the respective contact impedance or for analyzing the corresponding level of the respective contact impedance.

6. The electrode according to claim 1,
wherein the current delivering unit comprises at least one analog-to-digital converter,
wherein each analog-to-digital converter is configured to digitize the corresponding skin potential signal of the respective pin.

7. The electrode according to claim 1,
wherein the current delivering unit comprises a digital signal processor,
wherein the digital signal processor is configured to perform at least one of signal processing operations or calculations in order to estimate the corresponding range of the respective contact impedance with respect to the skin for each of the at least two pins or to analyze the corresponding level of the respective contact impedance with respect to the skin for each of the at least two pins, and
wherein the digital signal processor is configured to control the respective current delivery.

8. The electrode according to claim 7,
wherein the current delivering unit comprises at least one safety trigger,
wherein each safety trigger is configured to deactivate the corresponding pin if the respective current density with respect to the skin exceeds a predefined current density value,
wherein the digital signal processor is configured to control the at least one safety trigger and
wherein the digital signal processor is configured to receive the corresponding output signal of at least one analog-to-digital converter for performing at least one of the signal processing operations or the calculations.

9. The electrode according to claim 1,
wherein the current delivering unit comprises a communication unit,
wherein the communication unit is configured to transmit the corresponding results of estimating the corresponding range of the respective contact impedance with respect to the skin for each of the at least two pins or of analyzing the corresponding level of the respective contact impedance with respect to the skin for each of the at least two pins especially to a back-end unit.

10. The electrode according to claim 4,
wherein the communication unit is configured to transmit the corresponding status of the at least one safety trigger to a back-end unit.

11. The electrode according to claim 10,
wherein the communication unit is configured to receive configuration data for configuring the current delivering unit especially from the back-end unit.

12. The electrode according to claim 10,
wherein the respective communication with the aid of the communication unit is based on a wireline communication, and
wherein the respective communication with the aid of the communication unit is based on a wireless communication.

13. A method for transcranial current stimulation, the method comprising the steps of:
contacting the skin of a living or human being with the aid of at least two pins of an electrode,
estimating the corresponding range of the respective contact impedance with respect to the skin for each of the at least two pins or analyzing the corresponding level of the respective contact impedance with respect to the skin for each of the at least two pins with the aid of a current delivering unit connected to the at least two pins, and
selecting a set of the at least two pins for delivering a set of partial currents in order to achieve the desired current with the aid of the current delivering unit based on the estimated corresponding range of the respective contact impedance with respect to the skin for each of the at least two pins or based on the analyzed corresponding level of the respective contact impedance with respect to the skin for each of the at least two pins.

14. The method according to claim 13,
wherein the method further comprises the step of co-integrating the at least two pins and the current delivering unit into the electrode.

15. The method according to claim 13,
wherein the method further comprises:
predefining the desired current by a user and
selecting the set of the at least two pins in a manner that the corresponding contact impedance of at least one pin of said set with respect to the skin is lower than a predefined contact impedance value.

16. The electrode according to claim 1,
wherein the desired current is predefined by user, or
wherein the current delivering unit is configured to select the set of the at least two pins in a manner that the corresponding contact impedance of at least one pin of said set with respect to the skin is lower than a predefined contact impedance value.

17. The electrode according to claim 1,
wherein the current delivering unit comprises a digital signal processor,
wherein the digital signal processor is configured to perform at least one of signal processing operations or calculations to estimate the corresponding range of the respective contact impedance with respect to the skin for each of the at least two pins or to analyze the corresponding level of the respective contact impedance with respect to the skin for each of the at least two pins, or
wherein the digital signal processor is configured to control the respective current delivery.

18. The electrode according to claim 7,
wherein the current delivering unit comprises at least one safety trigger,
wherein each safety trigger is configured to deactivate the corresponding pin if the respective current density with respect to the skin exceeds a predefined current density value,
wherein the digital signal processor is configured to control the at least one safety trigger, or
wherein the digital signal processor is configured to receive the corresponding output signal of at least one analog-to-digital converter for performing at least one of the signal processing operations or the calculations.

19. The electrode according to claim 10,
wherein the respective communication with the aid of the communication unit is based on a wireline communication, or
wherein the respective communication with the aid of the communication unit is based on a wireless communication.

20. The method according to claim 13, wherein the method further comprises:
predefining the desired current by a user, or
selecting the set of the at least two pins in a manner that the corresponding contact impedance of at least one pin of said set with respect to the skin is lower than a predefined contact impedance value.

* * * * *